United States Patent [19]

Kamen

[11] Patent Number: 4,808,161

[45] Date of Patent: Feb. 28, 1989

[54] PRESSURE-MEASUREMENT FLOW CONTROL SYSTEM

[76] Inventor: Dean L. Kamen, 46 Gage Rd., Bedford, N.H. 03102

[21] Appl. No.: 22,167

[22] Filed: Mar. 5, 1987

Related U.S. Application Data

[63] Continuation-in-part of Ser. No. 836,023, Mar. 4, 1986.

[51] Int. Cl.$^4$ .............................................. A61M 5/00
[52] U.S. Cl. ............................. 604/67; 128/DIG. 12; 73/149; 604/251
[58] Field of Search .................. 604/65, 67, 251, 253, 604/247; 128/DIG. 12, DIG. 13; 73/149; 47/384–389, 395, 411

[56] References Cited

U.S. PATENT DOCUMENTS

| | | | |
|---|---|---|---|
| 2,116,636 | 5/1938 | Neumann | 73/149 X |
| 2,747,400 | 5/1958 | Fatio | 73/149 |
| 4,634,430 | 1/1987 | Polaschegg | 604/141 |

FOREIGN PATENT DOCUMENTS 0156211 10/1985 European Pat. Off. .
2110349 6/1972 France .
8404460 11/1984 PCT Int'l Appl. .

Primary Examiner—Stephen C. Pellegrino
Attorney, Agent, or Firm—Bromberg, Sunstein & Casselman

[57] ABSTRACT

A system is provided for controlling flow of a first fluid through a line. Dispensing means isolates a region of the first fluid in the line from effects of pressure in the line outside of the region and repetitively dispenses into and out of the region volume increments of first fluid. Measurement fluid housing means houses measurement fluid in communication with the region such that the dispensing of increments of first fluid into or out of the region causes a change in the measurement fluid pressure. Displacement means displaces a predetermined volume increment of measurement fluid into and out of the measurement fluid housing means, such that displacement of the predetermined volume increment causes a change in the measurement fluid pressure when the region is isolated by the dispensing means. Pressure measurement means measures changes in measurement fluid pressure. Control means, in communication with the pressure measurement means, the displacement means, and the dispensing means, causes the dispensing means to dispense first fluid in increments based on data from the pressure measurement means, such that at least one of the predetermined volume increments of measurement fluid displaced serves as a reference for the volume increments of first fluid outputted.

32 Claims, 8 Drawing Sheets

PRESSURE-MEASUREMENT FLOW CONTROL SYSTEM

This application is a continuation-in-part of application Ser. No. 836,023, filed Mar. 4, 1986.

DESCRIPTION

1. Field of Invention

The present invention relates to systems for controlling fluid flow, particularly in the area of medical infusion technology, although other embodiments are discussed below.

2. Background Art

Numerous devices exist in the prior art for controlling fluid flow for use in intravenous administration arrangements and similar applications. Many of these designs, including the design disclosed in U.S. Pat. No. 4,515,588, utilize elaborate systems for pressure regulation. The inventor is unaware, however, of any system which utilizes an external volume displacement arrangement for calibrating a dispensing arrangement that is monitored by a pressure-sensitive device.

DISCLOSURE OF INVENTION

A system is provided for controlling flow of a first fluid through a line. A region of first fluid in the line is isolated from external pressure effects, and a measurement fluid is housed in communication with the region in such a manner that the dispensing of volume increments of first fluid into or out of the region causes a change the pressure of the measurement fluid. The system measures the pressure of the measurement fluid when a predetermined volume increment of measurement fluid is displaced and when first fluid is inputted into or outputted out from the region. Based on this pressure data, the system determines the amount of fluid inputted or outputted, such that the predetermined increment of measurement fluid displaced serves as a reference for the volume increments of first fluid outputted.

BRIEF DESCRIPTION OF THE DRAWINGS

The foregoing objects and features of the invention are better understood with reference to the following description taken with the accompanying drawings in which.

DETAILED DESCRIPTION OF SPECIFIC EMBODIMENTS

Figure 1:
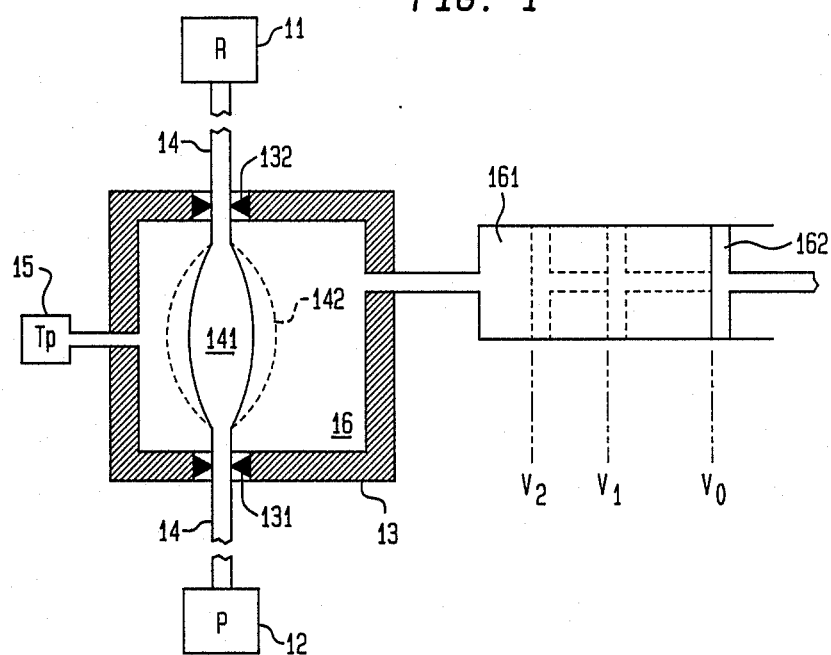
FIG. 1 is a simplified schematic of a first preferred embodiment of the invention.

FIG. 1 illustrates a fluid control system in accordance with the present invention for controlling fluid from a reservoir 11 into a patient 12. The fluid line 14 passes through a measurement housing 13 that is substantially airtight. The measurement housing 13 is provided with an upper valve 132 and a lower valve 131 for controlling flow into and out of flexible enclosure 141 located within the measurement housing. The portion of the interior 16 of the housing not occupied by the flexible enclosure 141 is filled with air. The interior 16 of the housing 13 is in communication with a volume standard that comprises a cylinder 161 in which travels a piston 162. The air pressure within the housing 13 is monitored by pressure trandsucer 15. It can be seen that the pressure in the interior 16 of the housing is a function of the volume occupied by flexible enclosure 141 and the effective volume of the interior 16 as modified by displacement of the piston 162 within the cylinder 161.

Study of FIG. 1 will reveal that displacement of the piston by some amount, for example 1 cc, from position $V_0$ to position $V_1$ removes 1 cc from the total effective volume of the interior 16 of the measurement housing 13. According to Boyle's Law, this decrease in volume results in a proportionate increase in air pressure in the interior 16; this increase is monitored by the pressure transducer 15. (Because the enclosure 141 is flexible, there is a concomitant increase in fluid pressure within the enclosure 141.) Let us assume that there is sufficient fluid in the enclosure 141 that it occupies the position shown in dashes as item 142. If the lower valve 131 is opened, fluid will drain from the enclosure shown as item 142 through the line 14 into the patient 12. Since valve 132 is closed, the walls of the flexible enclosure 142 will occupy a decreasing volume as the fluid leaves the enclosure, and at some point the decrease in volume occupied by the enclosure 142 will equal 1 cc. At this point, the pressure within the interior 16 of the measurement housing 13 has returned to the original pressure, since the total volume of the interior 16 that is available for occupancy by air has returned to the original volume. Thus the pressure transducer 15 can be used to determine when the original pressure has returned and can be used to establish the point in time when valve 131 should be closed in order for exactly 1 cc of fluid to have been dispensed into the patient. In this fashion, the volume standard that includes cylinder 161 and piston 162 serves as a template for determining the increment of fluid that may be dispensed through the flexible enclosure 141. The system may be restored to an initial position by retracting piston 162 to position $V_0$, and opening valve 132 until sufficient fluid flows into enclosure 141 that again the pressure indicated by transducer 15 has returned to the original level.

Figure 2:
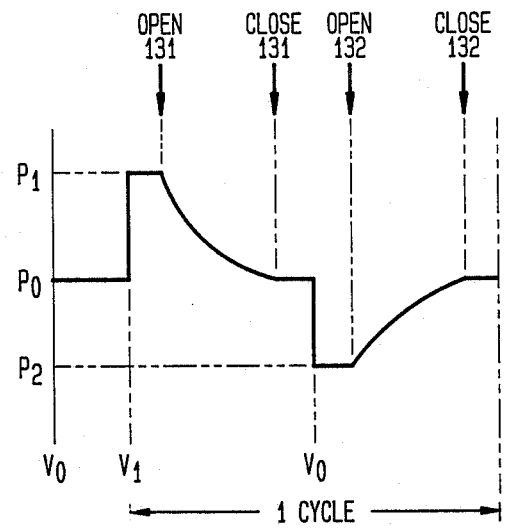
FIGS. 2-4 illustrate operation of the embodiment of FIG. 1.
Figure 3:
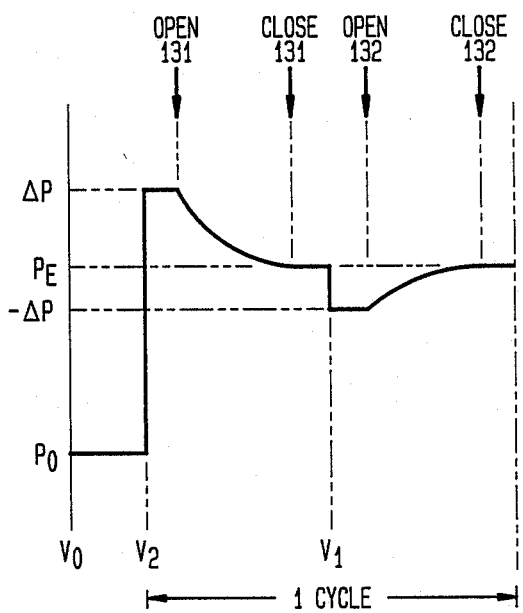
Figure 4:
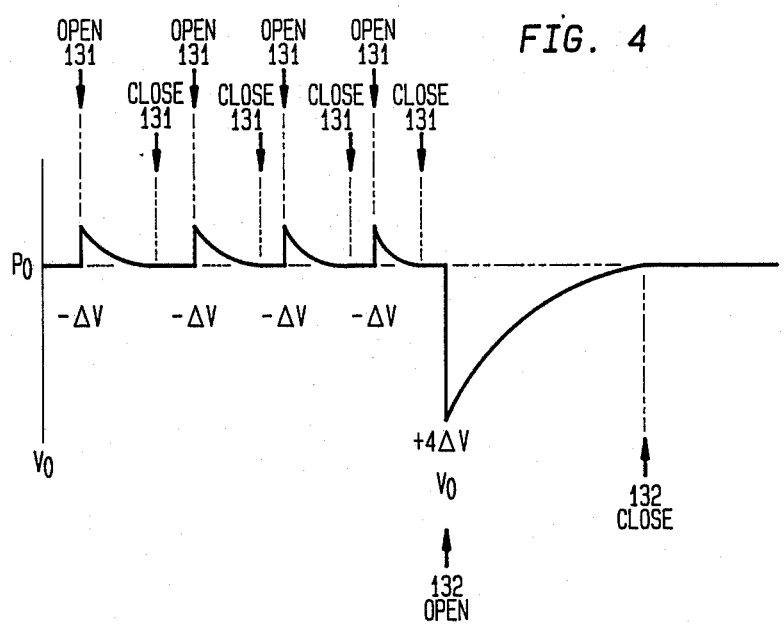

This cycle is illustrated in the graphs of FIGS. 2-4. In FIG. 2, atmospheric pressure is indicated by $P_0$. When the volume shrinks from $V_0$ to $V_1$ the pressure immediately rises to a new pressure $P_1$. After a desired interval, valve 131 is opened, and the pressure within the interior 16 of the measurement housing 13 is permitted to return to pressure $P_0$, at which point valve 131 is closed. Thus, there has been dispensed from flexible enclosure 141 a volume increment of fluid equal to $(V_0-V_1)$. After an additional desired interval, the piston 162 is returned to position $V_0$, at which point the pressure drops to amount $P_2$ in the interior 16. After another desired interval, the upper valve 132 is opened and the pressure is monitored until it returns to point $P_0$, whereupon valve 132 is closed and the same volume increment $(V_0-V_1)$ has been dispensed into flexible enclosure 141. After another desired interval, the cycle can begin again with displacement of the piston to position $V_1$ and so forth.

FIG. 3 illustrates that the same process shown in FIG. 2 may be conducted at an elevated pressure, so that the system acts in effect as a pump rather than merely a flow control device. In this embodiment atmospheric pressure indicated by $P_0$ is below the elevated operating pressure $P_E$. The piston 162 is used to displace volume from initial position $V_0$ to position $V_2$, whereupon the pressure in the interior 16 of the measurement housing 13 exceeds pressure $P_E$ by an amount $\Delta P$. When valve 131 is opened, the pressure is permitted to fall to $P_E$, and when after 131 is closed, the piston is not moved back to position $V_0$, but rather only to position $V_1$, so that pressure falls by an amount $\Delta P$ from $P_E$, but does not reach $P_0$. In this fashion pressure is maintained within a predetermined limit $\Delta P$ of the desired elevated pressure $P_E$.

In connection with FIGS. 2 and 3 it may be remarked that in fact the relation between pressure and volume is also a function of temperature, and that compression of the air by piston 162 would also cause a momentary increase in temperature of the air within the measurement housing 13 and that the elevated temperature could lead to errors. In this regard, it is within the domain of the present invention to monitor the temperature change and compensate the pressure system for temperature effects. However, I have conducted experiments and performed calculations that indicate that relatively high accuracy (measurement of volume within a percent or so) can be achieved without temperature compensation. It should also be noted that points $P_1$ and $P_2$ are somewhat arbitrary, and that, therefore, as long as the pressure transducer in any form, and the accuracy of the system will tend to be limited by the reproducibility of the volume displacements caused by piston 162.

Figure 8:
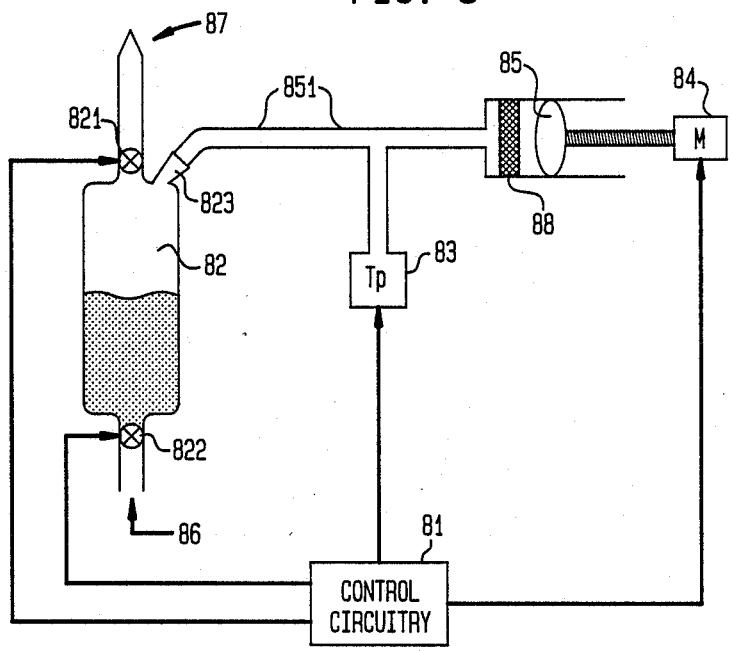
FIG. 8 shows a schematic diagram of the system illustrated in FIGS. 5 and 6.

Further, it would be possible within the spirit of the invention to introduce into the path of measurement flow flow a heat sink, i.e., a region of material with a high specific heat. One such structure is shown in FIG. 8. Element 88 is located within the piston-and-cylinder arrangement used to displace the predetermined volume of measurement fluid. In this particular embodiment, element 88 is a porous plug made of sintered stainless steel or other similar material. The plug serves both as a heat sink and as a filter to prevent migration of particles from the drive mechanism into the measurement fluid housing. The utility of the filter function may be especially important if line 851 is removably attachable to the piston-and-cylinder arrangement, since otherwise the cylinder may be exposed to foreign matter when the line 851 is detached. It will be seen that although a porous plug is shown, it would be possible to arrange material with a high specific heat surrounding the measurement fluid path rather than actually in the path.

FIG. 4 illustrates another mode of operation of the system. In this mode, the piston 162 of FIG. 1 is repeatedly displaced to the left in small increments $\Delta V$. Each time the resulting pressure increase from $P_0$ is thereafter cancelled out by opening valve 131 until the pressure returns to $P_0$, whereupon valve 131 is closed. In this fashion, an amount of fluid $\Delta V$ is dispensed each time through the fluid line. At some point after the piston has fully traversed its stroke to the left, valve 131 is closed for the last time, the piston is moved to the right, returning the system to volume $V_0$, at which point the upper valve 132 is opened, the flexible enclosure 141 is refilled, and upper valve 132 is closed when pressure again returns to $P_0$. Numerous other configurations are possible, the point being only that the piston 162 and cylinder 161 permit calibration of the dispensing system, the pressure of which can be monitored by a pressure transducer 15.

The foregoing discussion has assumed that, in the completion a measurement cycle of the system, the pressure is returned exactly to the initial pressure $P_0$. In practice, it is difficult to operate the valves 131 and 132 so as to achieve a return to the exact initial pressure. This fact generally does not matter, however, because Boyle's Law can be used to compute a correction factor. Boyle's Law provides that the product of pressure and volume occupied by a gas is constant. Let $P_0$ equal the intial air pressure inside the system, and $V_0$ equal the volume occupied by air in the system, and assume that a piston displacement of volume $\Delta V$ causes a pressure increment of $\Delta P$ in the system. The $P_0V_0=(P_0+\Delta P)(V_0+\Delta V)$. $P_0$ is, of course, measured by the pressure transducer in the system. $V_0$ can be determined in a set-up calibration step in the following manner. First, however, let it be noted that the piston may be driven by a stepper motor, each step of which causes the piston to displace a known volume v. The in $N_0$ steps are used in the calibration, $\Delta V = -N_0v$, and $V_0=[(P_0+\Delta P)(N_0v)]/\Delta P$, so that measuring the pressure rise $\Delta P$ attributable to the $N_0$ steps can give information sufficient to calculate $V_0$. This quantity is necessary in the correction factor, which may be determined by recognizing that the change in volume $\Delta V_i$ occupied by air in the system at the completion of a measurement cycle is a function solely of the change in volume of the system effected by piston displacement, by the stepper motor after $N_i$ steps, plus the volume flow $F_i$ of fluid that has left the system in a given measured cycle:

$$\Delta V_i = -N_i v + F_i$$

Assuming initial pressure $P_i$ and volume $V_i$ at the beginning of the measurement cycle, we have from Boyle's Law, $$P_iV_i=(P_i+\Delta P_i)(V_i-N_iv+F_i).$$

Solving for $F_i$ $$F_i=N_iv-\Delta P_iV_i/(P_i+\Delta P_i)$$

Again using Boyle's Law, we know that $$V_i=P_0V_0/P_i,$$

so that substituting in the preceding equation, we have $$F_i=N_iv-\Delta P_iP_0V_0/(P_i+\Delta P_i)P_i$$

The total fluid flow is, of course, the sum of the volume $F_i$ determined for each cycle, Since $N_iv$ is the volume of piston displacement over each cycle, the second term in the equation immediately above can be viewed as a correction term attributable to the difference in pressure obtaining at the beginning and end of a measurement cycle. When $\Delta P_i$ is zero, the correction term is zero. $P_0$ is assured at the beginning of the set-up calibration cycle, and $V_0$ is calculated with data from the calibration cycle as discussed above.

Using the above approach, the difference between the beginning and ending pressures for a given cycle no longer matters; the pressures are simply measured and used in the above equation to compute the correction term. Almost all system errors are cancelled, because the calibration cycle uses the system itself to calculate all important parameters.

Although the illustration has been made using air as the measurement field in the interior 16 of the meaurement housing 13, other fluids, including other gases and other liquids, may also be feasibly utilized.

A further mode is possible wherein after region 141 is filled by opening valve 132, and this valve is closed, the position of piston 162 is adjusted to create an internal pressure in the system such that, when valve 131 is opened, the fluid pressure at the infusion needle site is in equilibrium with ambient pressure. In this mode, with valve 131 opened, the delivery of fluid may be effected directly by moving piston 162 to the left, and reverse pumping may be effected by moving piston 162 to the right.

It should also be noted that the pressure transducer produces more information than simply departures from equalibrium pressure $P_0$ or $P_E$. In particular, the slope of the curve in these figures may also be monitored, thereby providing an extremely accurate system for determining on an instantaneous basis the flow rate. In fact, flow rate can be monitored so that a sudden decrease from a statistically determined average flow rate (i.e., slope of the pressure versus time curve) for a given patient can be used for causing the system to enter an alarm state indicating, for example, that the needle is no longer in the vein, or that there is an occlusion in the fluid line. That is, a sudden decrease in the rate of change of pressure with time during the flow portion (valve 131 open) of the cycle may be used as an indication of infiltration or occlusion. On the other hand, during the fill portion of the cycle (valve 132 open), the pressure comes to equilibrium at a level indicative of the height of the reservoir fluid head, and this pressure may be monitored to determine, on a substantially continuous basis, the level of fluid in the reservoir. In the event that during the fill portion of the cycle, the equilibrium pressure fails to materialize, then an upstream occlusion is indicated. The horizontal portions of the curves in FIG. 2 and 3 may also be used to monitor the system for air leaks and related phenomena; that is, the elevated or depressed pressures will not remain constant in the presence of such leaks.

The arrangement described above also permits detecting the presence of air in the fluid line. Under such circumstances, the pressure change when the volume is changed by piston 162 will be smaller than in the case when fluid is properly flowing. For example, with respect to FIG. 2, in the presence of air within the flexible enclosure 141, the usual threshold $P_1$ will not be reached when the volume changes to $V_1$. The failure to achieve the normal pressure differential can be viewed as an alarm state. However, since the valve arrangement 131 and 132 is quite flexible, before entering the alarm state, vavle 131 may be retained in its closed position and the piston 162 could be displaced maximally to the left to cause a great increase in pressure in the interior 16 of the measurement housing 13 with valve 132 open, so as to cause enclosure 141 to shrink to minimum volume; thereafter, piston 162 can be moved back to the right and flexible enclosure 141 be permitted to expand again and the test repeated to see if the normal rise in pressure has occurred. If it has not occurred a second time, then the alarm state would be entered. Otherwise, the approach just described is a reasonable method of purging the enclosure 141 from minor air bubbles. All of this has been done without risk of harm to the patient, since valve 131 has remained closed.

Although the system has been described as appropriate for controlling flow from a reservoir into a patient, this system may also be used for monitoring fluid flow out from a patient, for example in the measurement of urine volume. In such an embodiment, item 11 would constitute the catheter or other connection to the patient and item 12 of FIG. 1 would constitute a reservoir. Valve 131 would be closed while valve 132 could be opened. Periodically, valve 132 would be closed and then a measurement cycle such as illustrated in FIG. 2 would be performed to dispense a determined amount of fluid from the enclosure 141.

It should be noted that FIG. 1 also provides a simple arrangement for measuring the blood pressure of the patient. In this arrangement, the upper valve 132 is closed, and lower valve 131 is opened and the system is permitted to reach equilibrium. In this fashion, the pressure in line 14 is indicative of the patient's blood pressure, which may be monitored by pressure transducer 15.

Figure 5:
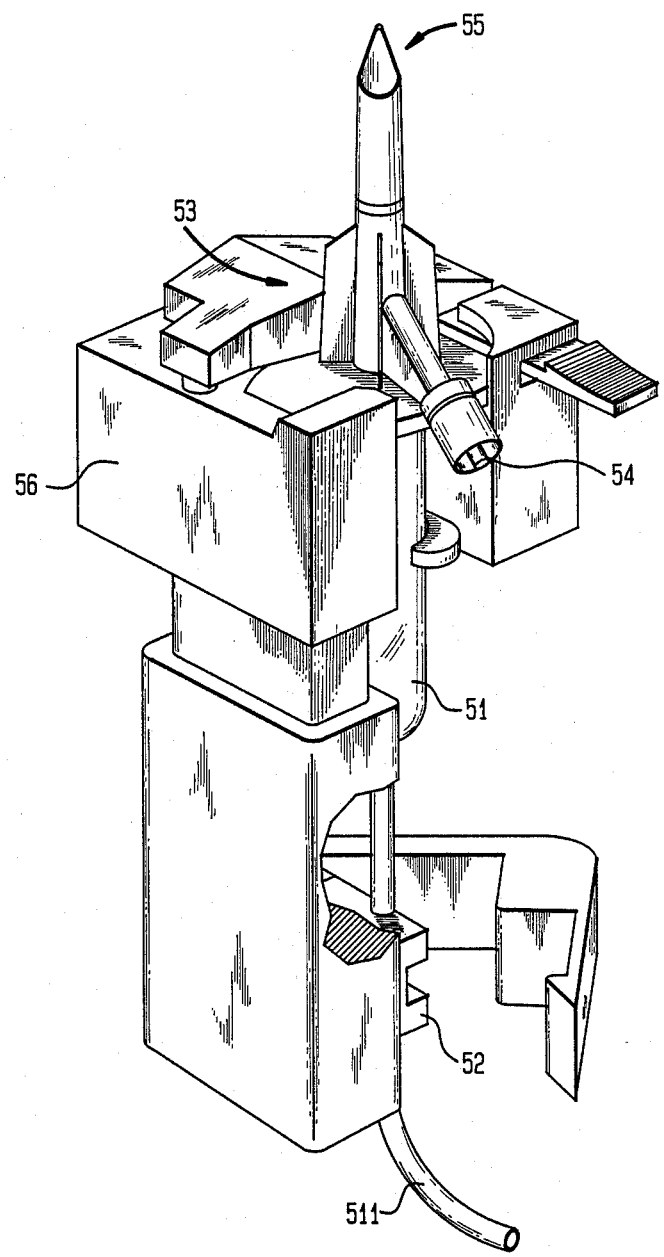
FIGS. 5 and 6 show different perspective views of a second preferred embodiment of the invention.

Although the invention has been described thus far with a separate measurement housing 13, such a housing may be combined with a drip chamber, as illustrated in FIG. 5. In FIG. 5 one may see a drip chamber 51 including a spike end 55, a fluid line end 511 that is held in a case 56. The drip chamber is provided with a fitting 54 for attachment both to a pressure transducer such as indicated by item 15 in FIG. 1 and to a volume standard including a piston 162 and cylinder 161 such as illustrated in FIG. 1. The volume standard can cause changes in the air pressure within the drip chamber 51 in the same fashion discussed above in connection with FIG. 1, except that the pressure changes are directly transmitted to the fluid, rather than through the intermediary of the flexible enclosure 141. The case 56 is provided with a valve in the lower region 52 of the drip chamber and another valve in the upper region 53 of the drip chamber. The valve in region 52 can be a normal crimp type valve operative on the fluid line. The upper valve 52 may be any suitable valve, although one is described in further detail in connection with FIGS. 6 and 7.

Figure 6:
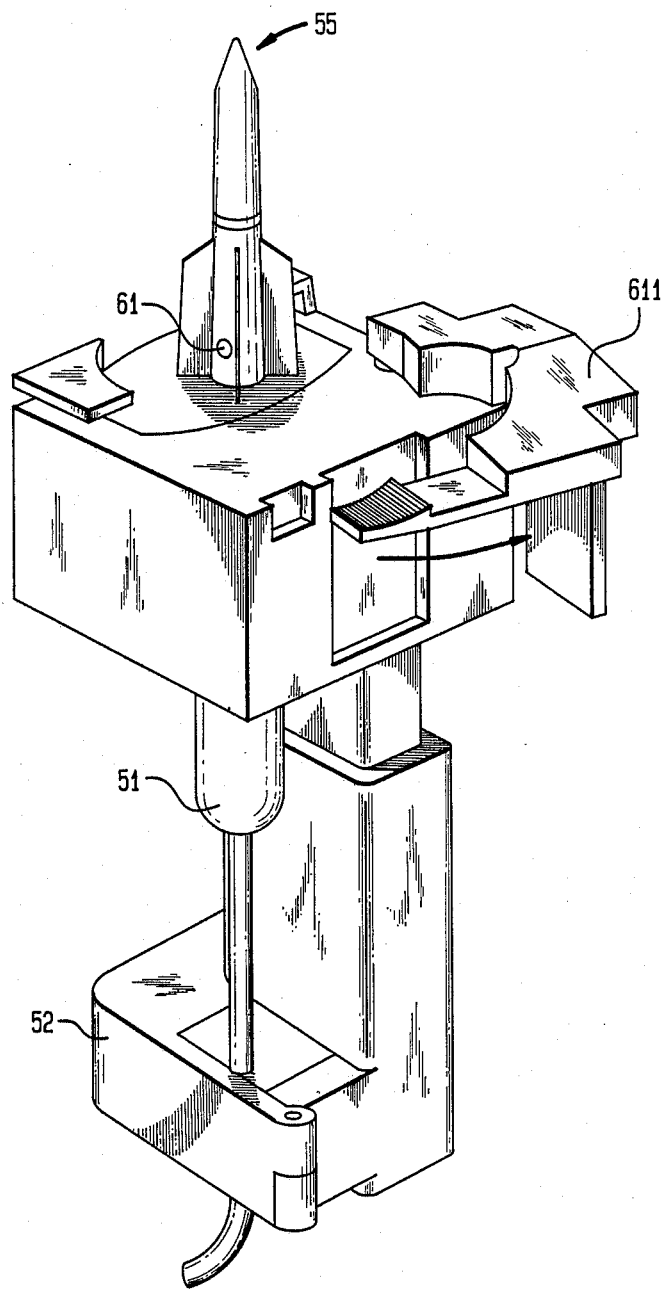

FIG. 6 presents another view of the system of FIG. 5. The drip chamber 51 in the spike end 55 is provided with a hole 61. The hole 61 is in the external rigid plastic portion of the drip chamber and would reach directly into the fluid line, except that the interior of the spike portion 55 is fitted with a piece of silicon rubber tubing, the outside walls of which engage tightly within the inside walls of the spike. Thus, hole 61 provides direct access to the outer wall of the silicon tubing but is outside the fluid flow path from the tip of spike 55 into the drip chamber 51. The upper valve actuator housing 611, however, contains an actuator pin which is capable of moving into and out of the hole 61 in such fashion as to squeeze the silicon tubing when the pin is in the closed positon. In this fashion flow through the spike 55 is halted when the pin is in the closed position. When the pin is in the open position, flow is permitted through spike 55. In this embodiment the silicon tubing, the hole 61, and the pin in upper valve actuator housing 611 provide an upper valve.

Figure 7:
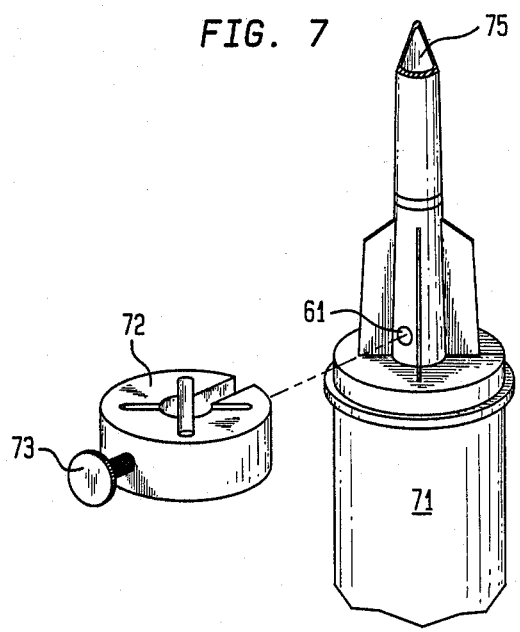
FIG. 7 shows a detailed drawing of a drip chamber for use in the embodiment of FIGS. 5 and 6.

As illustrated in FIG. 7, the upper valve access hole 61 may be provided with a manual adjustment in lieu of the automatic system described in connection with the previous figures. In the manual adjustment embodiment, adjustment ring 72 may be inserted over the spike end 75 until the thumb screw 73 can be turned to cause the inside portion of the screw to enter hole 61 and compress the silicon tube inside the spike 75. The degree of compression of the tube will regulate the flow through the spike 75. When the manual adjustment ring assembly 73 is removed from the spike, it may be used in the system of FIGS. 5 and 6.

The system of FIGS. 5 and 6 is illustrated schematically in FIG. 8, where there is shown the drip chamber 82 having spike end 87, upper valve 821, and lower valve 822, which valves are operated by control circuitry 81. A piston arrangement 85 compresses air in line 851, which is connected at fitting 823 into the drip chamber 82. Pressure in the interior of the drip chamber 82 is monitored by transducer 83, which is also connected to control circuitry 81. Motor 84 drives piston 85 in any of a variety methods well known in the art. The motor 84, which is also connected to control circuitry 81, may, for example, be a stepper motor which drives the piston by a conventional rack and pinion arrangement. In this fashion the control circuitry 81 will always know the relative position of the piston 85. Alternating sensing arrangements may utilize a simpler motor with Hall effect devices, for example, to monitor position of the rack. The cycles of operation of this system are identical to those as discussed above in connection with FIG. 1.

It should be noted that the embodiments of FIG. 1 and FIG. 8 can be used to determine the volume of fluid in the flexible enclosure 141 and the drip chamber 82 by a related but somewhat different technique. In particular one may cause a slight perturbation in volume by the piston 162 or 85. If the resulting increase in pressure is measured by the pressure transducer 15 or 83, Boyle's Law may be used directly in order to determine the volume of fluid in the drip chamber or the flexible enclosure. This approach could be used to determine the volume of fluid in any flexible enclosure in the case of FIG. 1 or in any rigid enclosure in the case of FIG. 8.

Figure 9A:
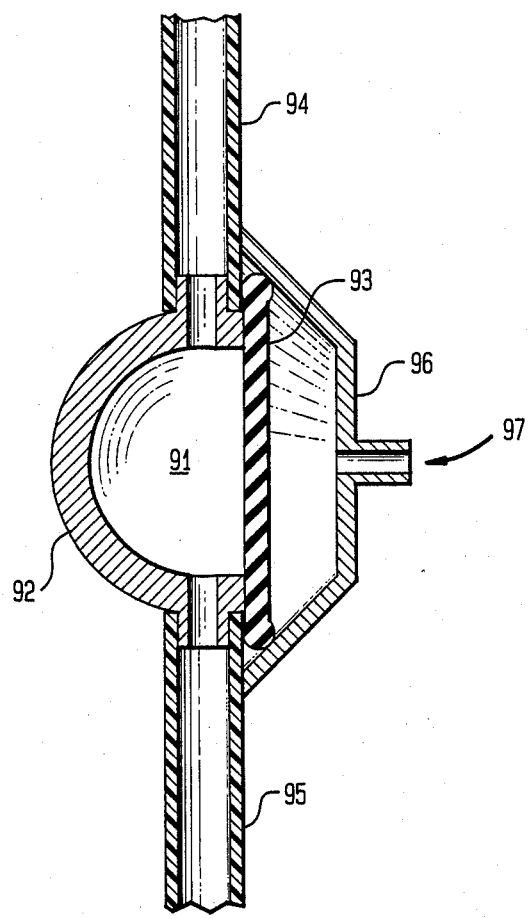
FIGS. 9A and 9B show a third preferred embodiment of the invention.
Figure 9B:
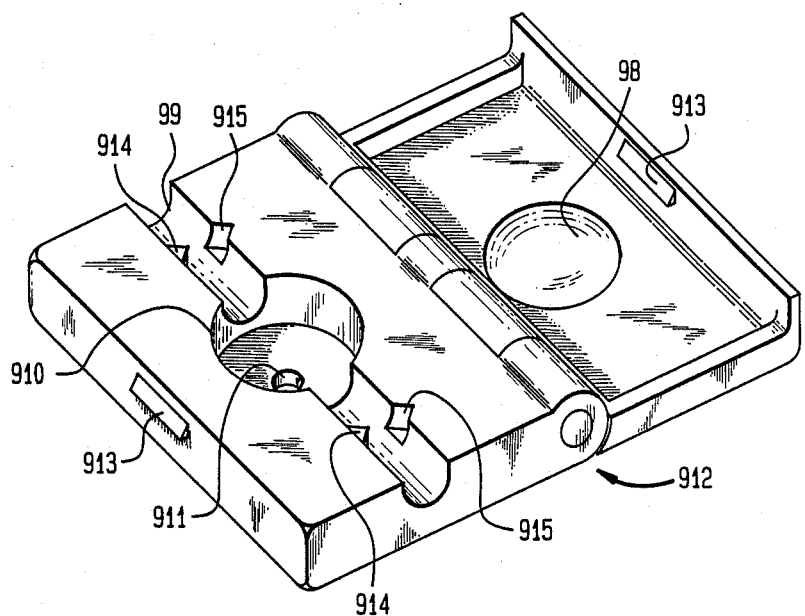

FIGS. 9A and 9B show an alternative preferred embodiment of the invention. The region of fluid in the line to be isolated 91 is defined by hemispherical rigid enclosure 92, flexible diaphragm 93, and the region of the input line 94 and output line 95 below and above the valving means. The measurement fluid is housed by a rigid shell 96, which includes a connector 97 to the displacement means. A hemispherical shape was chosen for rigid enclosure 92 because this particular shape was found to exhibit the least deformation when subject to pressure, and thus would eliminate deformation as a possible source of system error.

FIG. 9B shows a housing for the structure shown in FIG. 9A. The hemispherical rigid enclosure 92 seats in recess 98; input and output lines, 94 and 95, seat in trough 99; shell 96 seats in hollow 910; and connector 97 seats in mating fitting 911. Valving of the input and output lines is accomplished by wedges 99, which push into and retract out of mating receptacles 914. The unit closes around hinge 912, and is held shut by clasp 913.

Figure 10A:
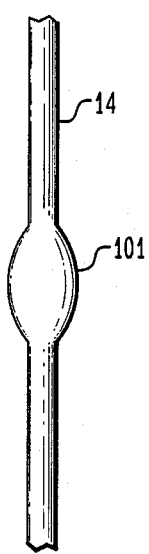
FIGS. 10A, 10B and 10C show a fourth preferred embodiment of the invention.
Figure 10B:
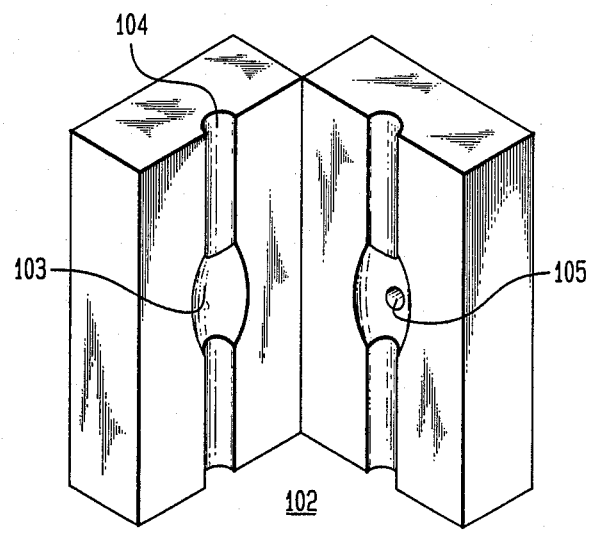
Figure 10C:
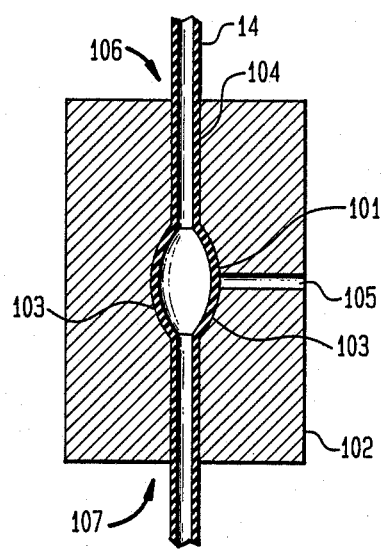

FIGS. 10A, 10B, and 10C show another preferred embodiment of the present invention. As shown in FIG. 10A, in this embodiment, the flexible enclosure is an integrally formed bulge 101 in tube 14. The bulged tube is contained in housing 102, which includes two complementary halves. Each half includes a hollow 103 to receive the bulge, and a trough to receive the non-bulged portion of tube 14. One of the two halves of housing 102 includes a port 105, through which passes the measurement fluid. FIG. 10C shows a cross section of the housing with the two halves fastened together and with the bulged tube in place. It is desirable for the upper portion 106 and lower portion 107 of the tube to be sealed against the inner surface of the housing to prevent leakage of measurement fluid. Valving means are affixed above and below housing 102, and means are provided for connected port 105 to displacement means.

A key advantage of the embodiment shown in FIGS. 10A, 10B, and 10C is that it is readily adaptable to intravenous infusion tubes currently in use. It has been found that bulge 101 can be readily formed in situ in the housing by heating the tube within the housing, and then increasing the air pressure within the tube. The tube material will become sufficiently malleable upon heating so as to become molded to the inside surface of the housing when the air pressure is increased. Further, the non-bulged portions of the tube will, as a result of heating and air pressure increase, become sealed to the inner surface of the housing, thus achieving the desired end structure. It has been found that after use, the tube can be readily removed from the opened housing by gentle pulling.

What is claimed is:

1. A system for controlling flow of a first fluid through a line, the system comprising:
    dispensing means (i) for isolating a region of the first fluid in the line from effects of pressure in the line outside of the region, the region having an input and an output for the first fluid, and (ii) for repetitively dispensing into and out of the region volume increments of first fluid;
    measurement fluid housing means for housing measurement fluid in communication with the region such that the dispensing of increments of first fluid into or out of the region causes a change in the measurement fluid pressure;
    displacement means for displacing a predetermined volume increment of measurement fluid into and out of the measurement fluid housing means, such that displacement of the predetermined volume increment causes a change in the measurement fluid pressure when the region is isolated by the dispensing means;
    pressure measurement means for measuring changes in measurement fluid pressure; and
    control means, in communication with the pressure measurement means, the displacement means, and the dispensing means, for causing the dispensing means to dispense first fluid in increments based on data from the pressure measurement means, such that at least one of the predetermined volume increments of measurement fluid displaced serves as a reference for the volume increments of first fluid outputted.

2. A system according to claim 1, wherein the dispensing means includes an input valve at the first fluid input to the region and an output valve at the first fluid output from the region.

3. A system according to claim 2, wherein the measurement housing means is disposed in relation to the region so as to define collectively therewith a fixed volume that is varied by the displacement means, and wherein the region includes a flexible interface surface defining a boundary between the measurement fluid and the first fluid.

4. A system according to claim 3, wherein the region includes a rigid enclosure with an input, an output, and a window, the flexible interface surface covering the window.

5. A system according to claim 3, wherein the rigid enclosure is substantially hemispherical in shape.

6. A system according to claim 3, wherein the region includes a flexible tube, and the walls of the tube comprise the flexible interface surface.

7. A system according to claim 6, wherein the flexible tube includes a bulge with thinner walls than the remainder of the tube, and wherein the walls of the bulge comprise the flexible interface surface.

8. A system according to claim 7, further comprising a case in which the bulge is housed and having fluid-tight seals at the input and output of the tube.

9. A system according to claim 8, including means for forming the bulge inside of the case.

10. A system according to claim 3, wherein the control means includes means for causing the dispensing means to dispense first fluid in the same increments of volume as displaced by the displacement means.

11. A system according to claim 2, wherein the measurement fluid is a gas.

12. A system according to claim 11, wherein the gas is air.

13. A system according to claim 11, wherein the dispensing means includes a heat sink in communication with the measurement fluid for reducing gas that might otherwise affect system accuracy owing to pressure changes not attributable to volume changes in first fluid in the region or in measurement fluid.

14. A system according to claim 13, wherein the heat sink comprises a porous plug disposed between the displacement means and the region of isolated first fluid.

15. A system according to claim 14, wherein the porous plug is made of sintered stainless steel.

16. A system according to claim 11, wherein the dispensing means includes a drip chamber through which the first fluid flows and having an upper region that is in communication with the measurement fluid housing means.

17. A system according to claim 16, wherein the control means includes means for causing the dispensing means to dispense first fluid in the same increments of volume as displaced by the displacement means.

18. A system according to claim 1, wherein the displacement means includes a motor-driven cam drive.

19. A system according to claim 1, wherein the displacement means comprise bellows.

20. A system according to claim 1, wherein the displacement means comprises a piston arrangement.

21. A system according to claim 2, wherein control means includes means for controlling first fluid flow in accordance with a pumping cycle as follows:
(A) with input and output valves closed, actuating the displacement means to a predetermined negative volume increment to decrease the volume of measurement fluid;
(B) opening the output valve to let first fluid out of the region until the pressure measurement means indicates that the pressure of measurement fluid has returned to the pressure at the beginning of step (A), and then closing the output valve;
(C) activating the displacement means to displace a predetermined positive volume increment equal in absolute value to the foregoing negative increment;
(D) opening the input valve to admit first fluid until the pressure measurement means indicates that the pressure of the measurement fluid has returned to the pressure at the beginning of step (A), whereupon the cycle may be repeated.

22. A system according to claim 21, wherein the pressure of the measurement fluid at the beginning of step (A) is approximately at that of the ambient atmosphere.

23. A system according to claim 21, wherein the control means further includes means for detecting an occlusion in the first fluid line or infiltration of the intravenenous needle into surrounding tissue, the occlusion detection means comprising means for detecting an unusually slow pressure return in step (B) and step (D), such unusually slow pressure return being characteristic of an occlusion at the output or at the input or of infiltration of the intravenous needle into surrounding tissue.

24. A system according to claim 2, wherein control means includes means for controlling first fluid flow in accordance with a pumping cycle as follows:
(A) with input and output valves closed, calibrating the system by measuring pressure of the measurement fluid before and after the predetermined volume increment is displaced, storing these measurements, and then restoring the original volume and pressure of the measurement fluid;
(B) opening the output valve to let first fluid flow out of the region until the pressure measurement means indicates that the pressure of the measurement fluid has reached a value equal in absolute value to the absolute value of the pressure measured in step (A) after the displacement of the predetermined volume increment, and then closing the output valve;
(C) opening the input valve to let first fluid flow into the region until the pressure measurement means indicates that the pressure of the measurement fluid has reached a value equal to the pressure measure in step (A) before the displacement of the predetermined volume increment, and then closing the input valve, whereupon steps (B) and (C) may be repeated.

25. A system according to claim 2, wherein the control means includes means for controlling first fluid flow in accordance with a pumping cycle as follows:
(A) with input and output valves closed, activating the displacement means to displace a predetermined negative volume increment;
(B) opening the output valve to let first fluid out of the region until the pressure measurement means indicates that the pressure of the measurement fluid has returned to the pressure at the beginning of step (A), and then closing the output valve, whereupon the cycle may be repeated.

26. A method for controlling flow of a first fluid through a line, the method comprising the following steps:
(A) isolating a region of the fluid in the line from effects of pressure in the line outside of the region;
(B) housing a measurement fluid in communication with the region such that input and output of first fluid into and out of the region cause a change in the pressure of the measurement fluid;

(C) displacing a predetermined volume increment of measurement fluid;
(D) measuring the pressure of the measurement fluid; and
(E) inputting and outputting first fluid into and out of the region based on measurement fluid pressure data obtained in step (D), such that the predetermined increment of measurement fluid displaced serves as a reference for the amount of first fluid outputted.

27. A method for controlling flow of a first fluid through a line, the method comprising the following steps:
(A) isolating a region of the first fluid in the line from effects of pressure in the line outside of the region;
(B) housing a measurement fluid in communication with the region such that a change in volume of the first fluid in the region causes a change in the pressure of the measurement fluid;
(C) inputting and outputting liquid into and out of the region while displacing a predetermined volume increment of measurement fluid and maintaining a substantially constant measurement fluid pressure.

28. A method for controlling flow of a liquid through a line, the method comprising the following steps:
(A) isolating a region of the liquid in the line from effects of pressure in the line outside of the region;
(B) housing a measurement gas in communication with the region such that changes in volume of the liquid in the region cause a proportionate change in the pressure of the measurement gas;
(C) measuring the pressure of the measurement gas before and after the volume of the gas is changed by a predetermined amount while the volume of liquid in the region remains substantially constant;
(D) inputting and outputting liquid into and out of the region based on the data obtained in step (C) and o measurement of the pressure of the measurement gas while liquid is being inputted and outputted into and out of the region.

29. A method for monitoring blood pressure in a patient, comprising the following steps:
(A) isolating a region of intravenous fluid in an intravenous line from effects of pressure in the line outside of the region;
(B) housing a measurement gas in communication with the region such that changes in volume of the fluid in the region cause a proportion change in the pressure of the measurement gas;
(C) measuring the pressure of the measurement gas before and after the volume of the gas is changed by a predetermined amount while the volume of intravenous fluid in the region remains substantially constant;
(D) measuring the pressure of the measurement gas before and after the volume of the gas is changed by a predetermined amount while the output from the region to the patient is open;
(E) calculating the blood pressure in the patient based on a comparison of the data obtained in steps (C) and (D).

30. A method for detecting occlusion in an intravenous line or infiltration of an intravenous needle into surrounding tissue, comprising the following steps:
(A) isolating a region of intravenous fluid in an intravenous line from effects of pressure in the line outside of the region;
(B) housing a measurement gas in communication with the region such that changes in volume of the fluid in the region cause a proportionate change in the pressure of the measurement gas;
(C) measuring the pressure of the measurement gas before and after the volume of the gas is changed by a predetermined amount while the volume of intravenous fluid in the region remains substantially constant;
(D) inputting and outputting liquid into and out of the region based on the data obtained in step (C) and on measurement of the pressure of the measurement gas while liquid is being inputted and outputted into and out of the region;
(E) causing an alarm state to be entered into if there is detected a substantial delay in change of pressure of the measurement gas in response to actuated input or output of intravenous fluid, such delay being characteristic of occlusion in the intravenous line or infiltration of surrounding tissue by the intravenous needle.

31. A method for measuring first fluid output along a line, comprising the following steps:
(A) isolating a region of the fluid in the line from effects of pressure in the line outside of the region;
(B) housing a measurement fluid in communication with the region such that input and output of first fluid into and out of the region cause a change in the pressure of the measurement fluid;
(C) displacing a predetermined volume increment of measurement fluid;
(D) measuring the pressure of the measurement fluid; and
(E) calculating the volume of first fluid output along the line based on data obtained from the measurement of the pressure of the measurement fluid when a predetermined increment of measurement fluid is displaced and during movement of first fluid into and out of the region, such that the predetermined increment of measurement fluid displaced serves as a reference for the amount of first fluid outputted.

32. A system according to claim 11, wherein the control means includes means for controlling first fluid flow in accordance with a pumping cycle as follows:
(A) with input and output valves closed, calibrating the system by measuring pressure $P_0$ of the measurement fluid, displacing a predetermined volume increment $N_0v$ of measurement fluid, determining the resulting change in pressure $\Delta P_0$ and deriving the chamber volume $V_0$ using the relation $$V_0 = (P_0 + \Delta P_0) N_0 v / \Delta P_0;$$

(B) with input valve closed, measuring the pressure $P_i$, and causing the displacement means to displace a volume $N_iv$ of measurement fluid, where $N_iv$ can be zero, positive or negative;
(C) opening the output valve to let first fluid out of the region, and then measuring the resulting pressure at a given time, and determining the change from $P_i$ in pressure $\Delta P_i$ at the given time;
(D) calculating the volume flow $F_i$ of first fluid out of the region from the beginning of the cycle in step (B) to the given time in accordance with the relation $$F_i = N_{iil\ v} - \Delta P_i P_0 V_0 / (P_i + \Delta P_i) P_i$$

whereupon the cycle beginning in step (B) may be repeated.